US012558460B2

(12) United States Patent
Kim et al.

(10) Patent No.: US 12,558,460 B2
(45) Date of Patent: Feb. 24, 2026

(54) POROUS INORGANIC PARTICLE, AND COMPOSITE FILLER, PRODUCT USING THE SAME

(71) Applicant: LG CHEM, LTD., Seoul (KR)

(72) Inventors: Yunseop Kim, Daejeon (KR); Lucia Kim, Daejeon (KR); Jee Seon Kim, Daejeon (KR)

(73) Assignee: LG CHEM, LTD., Seoul (KR)

( * ) Notice: Subject to any disclaimer, the term of this patent is extended or adjusted under 35 U.S.C. 154(b) by 210 days.

(21) Appl. No.: 18/560,156

(22) PCT Filed: Mar. 6, 2023

(86) PCT No.: PCT/KR2023/003039
§ 371 (c)(1),
(2) Date: Nov. 10, 2023

(87) PCT Pub. No.: WO2023/182700
PCT Pub. Date: Sep. 28, 2023

(65) Prior Publication Data
US 2024/0207489 A1      Jun. 27, 2024

(30) Foreign Application Priority Data
Mar. 24, 2022     (KR) ........................ 10-2022-0036793

(51) Int. Cl.
*A61L 27/56* (2006.01)
*A61L 27/12* (2006.01)
(Continued)

(52) U.S. Cl.
CPC .............. *A61L 27/56* (2013.01); *A61L 27/12* (2013.01); *A61L 27/46* (2013.01); *C01B 25/32* (2013.01);
(Continued)

(58) Field of Classification Search
None
See application file for complete search history.

(56) References Cited

U.S. PATENT DOCUMENTS 5,037,543 A      8/1991  Maejima et al.
2007/0053814 A1  3/2007  Kobayashi et al.
(Continued)

FOREIGN PATENT DOCUMENTS

CN      1101544 A      4/1995
CN      101337665 B    4/2011
(Continued)

OTHER PUBLICATIONS

English language translation of CN 113460986 A, Publ. Oct. 1, 2021. (Year: 2021).*
(Continued)

*Primary Examiner* — Dominic Lazaro
(74) *Attorney, Agent, or Firm* — ROTHWELL, FIGG, ERNST & MANBECK, P.C.

(57) ABSTRACT

The present disclosure relates to a porous inorganic particle which comprises a sintered body of calcium-based particles, and pores distributed in the sintered body, and has a core-shell structure of a core having a high porosity and a shell having a porosity lower than that of the core, wherein the calcium-based particles comprise first calcium-based particles having a maximum diameter of 10 nm to 500 nm, and second calcium-based particles having a maximum diameter of 1 μm to 10 μm, and to a composite fillers and product using the same.

20 Claims, 2 Drawing Sheets

(51) Int. Cl.

| | |
|---|---|
| *A61L 27/46* | (2006.01) |
| *C01B 25/32* | (2006.01) |

(52) U.S. Cl.

CPC ....... *A61L 2430/34* (2013.01); *C01P 2004/03* (2013.01); *C01P 2004/32* (2013.01); *C01P 2004/84* (2013.01); *C01P 2006/12* (2013.01); *C01P 2006/14* (2013.01); *C01P 2006/21* (2013.01)

(56) References Cited

U.S. PATENT DOCUMENTS

| | | |
|---|---|---|
| 2009/0041812 A1 | 2/2009 | Bell |
| 2016/0338918 A1 | 11/2016 | Bell |
| 2019/0209737 A1 | 7/2019 | Zihlmann |
| 2020/0069839 A1 | 3/2020 | Kim et al. |
| 2022/0235221 A1 | 7/2022 | Lee et al. |

FOREIGN PATENT DOCUMENTS

| | | | |
|---|---|---|---|
| CN | 106115642 A | 11/2016 | |
| CN | 106115646 B | 1/2018 | |
| CN | 111803715 A | 10/2020 | |
| CN | 113460986 A * | 10/2021 | ........... A61K 9/1611 |
| JP | 2573825 B2 | 1/1997 | |
| JP | 2006-176371 A | 7/2006 | |
| JP | 2007-070211 A | 3/2007 | |
| KR | 10-2020-0076754 A | 6/2020 | |
| KR | 10-2266385 B1 | 6/2021 | |
| RU | 2303580 C2 | 7/2007 | |
| RU | 2497548 C1 | 11/2013 | |
| TW | 201927348 A | 7/2019 | |
| WO | 2009-021209 A2 | 2/2009 | |

OTHER PUBLICATIONS

Office Action dated Dec. 13, 2024, of the corresponding Australian Patent Application No. 2023239927, 3 pages.

Zaitseva et al., "Studying and Assessing the Toxicity of Calcium Oxide Nanoparticles under One-Time Inhalation Exposure", Nanotechnologies in Russia (2019) vol. 14, Nos. 9-10, pp. 497-503.

Okeke et al., "The use of calcium carbide in food and fruit ripening: Potential mechanisms of toxicity to humans and future prospects," Toxicology (2022) vol. 468, 153112, pp. 1-12.

Kadyrova et al., "Biological properties and synthesis of complex salts of a-amino acids of biogenic metals", Monograph (2014) Kazan: Kazan, State Energy Univ., 8 pages with English abstract.

International Search Report issued for International Application No. PCT/KR2023/003039 on Jun. 9, 2023, 4 pages.

Zhou et al., "Synthesis, sintering and characterization of porous nano-structured CaP bioceramics prepared by a two-step sintering method", Ceramics International, vol. 41, No. 3, Apr. 1, 2015, pp. 4696-4705.

* cited by examiner

[FIG.1]
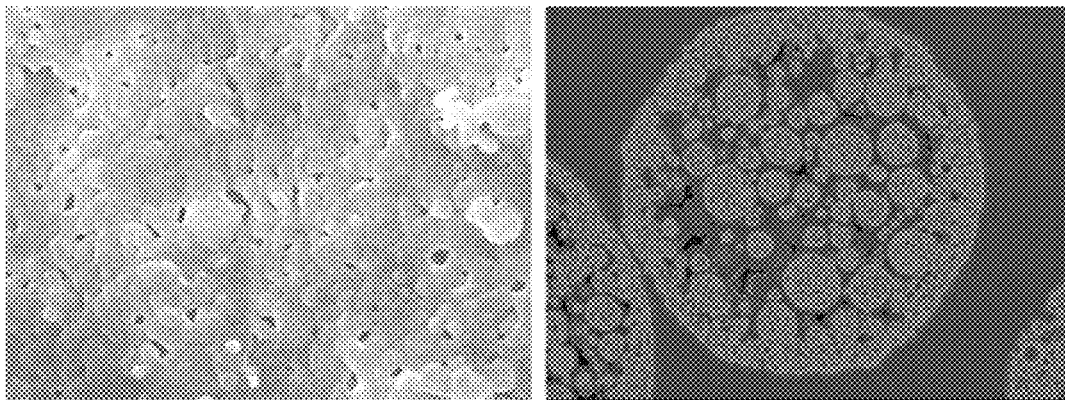
[FIG.2]
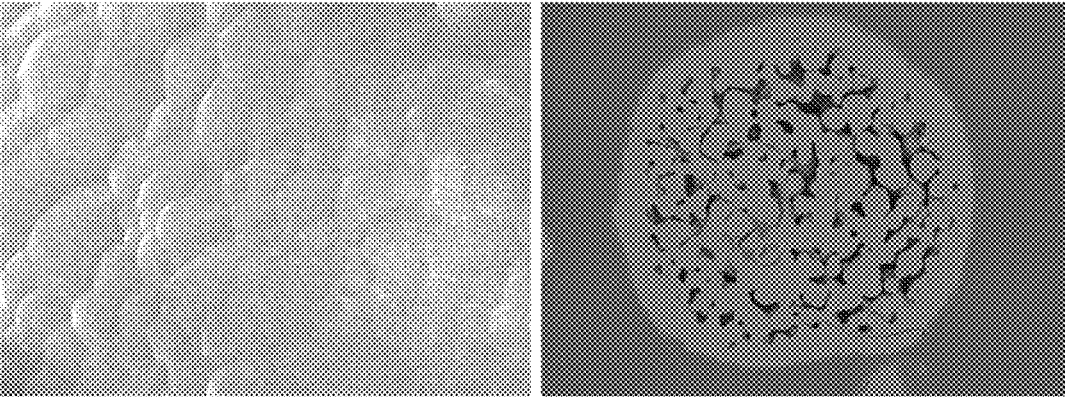
[FIG. 3]
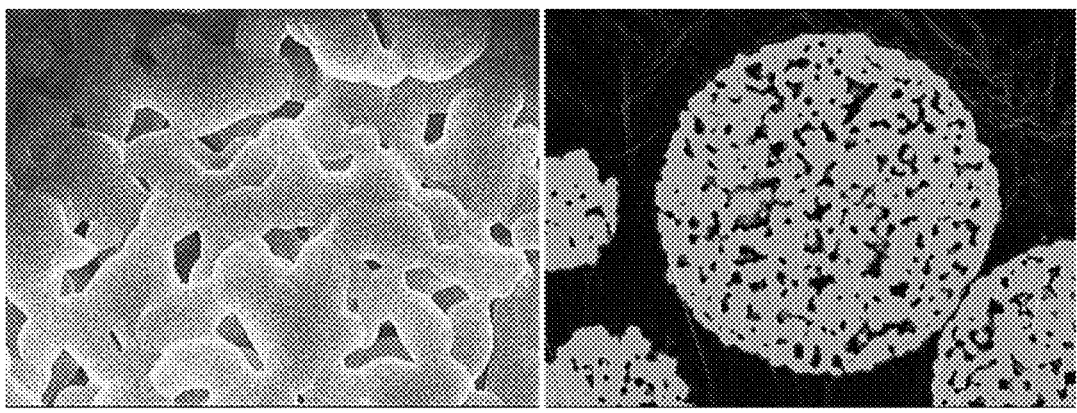

[FIG.4]
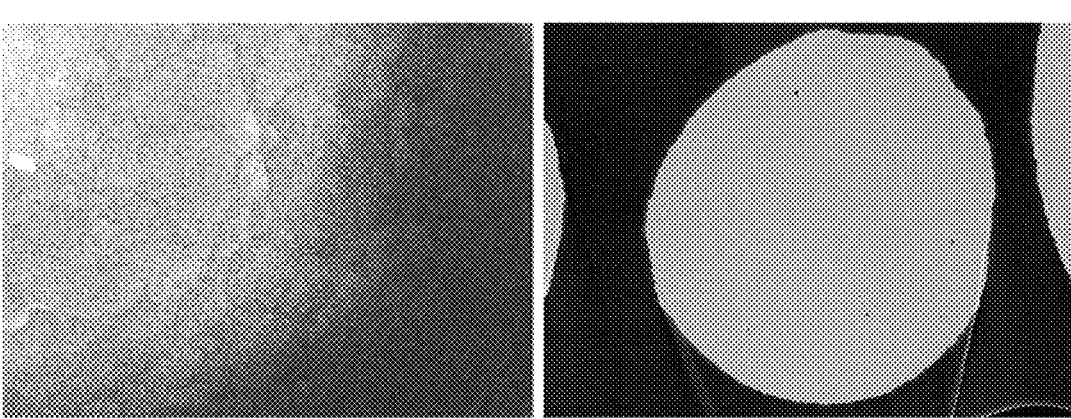

1

POROUS INORGANIC PARTICLE, AND COMPOSITE FILLER, PRODUCT USING THE SAME

CROSS-REFERENCE TO RELATED APPLICATION(S)

This application is a 35 U.S.C. § 371 National Phase Entry Application from PCT/KR2023/003039, filed on Mar. 6, 2023, which claims the benefit of Korean Patent Application No. 10-2022-0036793 filed on Mar. 24, 2022 with the Korean Intellectual Property Office, the disclosures of which are incorporated herein by reference in their entirety.

The present disclosure relates to a porous inorganic particle, and a composite fillers and product using the same.

TECHNICAL FIELD

Background

Filler is a supplementary material or content that is injected or inserted into wrinkles or indented scars, and is widely used for human organs such as wrinkles, scars, cosmetic surgery or vocal cords that are needed for maintaining a volume.

Fillers are classified as permanent, semi-permanent, and temporary depending on the length of time they remains in tissue, and specific examples thereof include collagen, fat, hyaluronic acid, hydroxyapatite, polymethacrylic acid, botox, and the like.

Hyaluronic acid filler, which is conventionally used, has the effect of satisfying voluminous feeling of an area to be treated, but it has a drawback that skin elasticity cannot be fundamentally improved, the decomposition rate is too fast and the filler maintaining period is short.

Further, the calcium filler not only promotes natural collagen production and has a fundamental skin improvement effect, but also has the advantage that decomposition rate is slow and the maintaining period is long, but has the drawback that the bioactivity is low and the skin improvement effect is exhibited slowly.

In order to overcome the limitations of such single-component fillers, a method has been proposed using a composite filler that is a mixture of a biocompatible polymer such as carboxymethylcellulose and calcium particles. The composite filler of carboxymethyl cellulose and calcium particle overcomes the limitation of single-component filler, and maintains an initial volume and then produces a natural collagen through tissue stimulation of calcium particles, thereby exhibiting the effect of improving skin itself.

However, calcium particles applied to composite fillers of carboxymethylcellulose and calcium particles which are conventionally used are spherical high-density solid particles with smooth surfaces, which have a limitation in low bioactivity. Further, there have been difficulties in orthodontic procedures due to the low biodegradability of carboxymethylcellulose.

Therefore, there is a demand for the development of a filler that has improved bioactivity as compared to existing calcium particles, rapidly exhibits skin improvement effects, and enables maintenance of initial volume and corrective procedures.

BRIEF SUMMARY

Technical Problem

It is an object of the present disclosure to provide a porous inorganic particle with high production efficiency and excellent bioactivity and strength.

It is another object of the present disclosure to provide a composite filler in which a porous inorganic particle produced by a method with high production efficiency is introduced into the composite filler to enhance the bioactive performance of the composite filler and improve the skin improvement effect, thus having high biodegradability and capable of corrective procedures.

It is yet another object of the present disclosure to provide a product using a composite filler having improved bioactivity.

Technical Solution

In order to achieve the above objects, provided herein is a porous inorganic particle which comprises a sintered body of calcium-based particles, and pores distributed in the sintered body, and has a core-shell structure of a core having a high porosity and a shell having a porosity lower than that of the core, wherein the calcium-based particles comprise first calcium-based particles having a maximum diameter of 10 nm to 500 nm, and second calcium-based particles having a maximum diameter of 1 μm to 10 μm.

Also provided herein is a composite filler comprising the porous inorganic particle: and a biodegradable carrier.

Further provided herein is a product comprising the composite filler.

DETAILED DESCRIPTION

Hereinafter, a porous inorganic particle according to specific embodiments of the disclosure, a composite filler and product using the same will be described in more detail.

Unless otherwise specified throughout this specification, the technical terms used herein are only for reference to specific embodiments and is not intended to limit the present disclosure.

The singular forms "a", "an", and "the" used herein include plural references unless the context clearly dictates otherwise.

The term "including" or "comprising" used herein specifies a specific feature, region, integer, step, action, element and/or component, but does not exclude the presence or addition of a different specific feature, region, integer, step, action, element, component and/or group.

The terms including ordinal numbers such as "a first", "a second", etc. are used only for the purpose of distinguishing one component from another component, and are not limited by the ordinal numbers. For instance, a first component may be referred to as a second component, or similarly, the second component may be referred to as the first component, without departing from the scope of the present invention.

Now, the present disclosure will be described in more detail.

1. Porous Inorganic Particles

According to one embodiment of the disclosure, there can be provided a porous inorganic particle which comprises a sintered body of calcium-based particles, and pores distributed in the sintered body, and has a core-shell structure of a core having a high porosity and a shell having a porosity lower than that of the core, wherein the calcium-based particles comprise first calcium-based particles having a maximum diameter of 10 nm to 500 nm, and second calcium-based particles having a maximum diameter of 1 μm to 10 μm.

The present inventors have found that the porous inorganic particle of one embodiment not only has higher porosity and specific surface area than those of existing high-density solid particles, and thus is improved in biological activity to quickly induce the treatment effect of fillers, but also has fast particle production speed, does not require a further drying steps to have high productivity, does not use organic solvents and thus is produced by a safe spray drying method without a risk of explosion, thereby maximizing production efficiency.

In particular, as the porous inorganic particle contains two types of calcium-based particles divided by the maximum diameter of the particles, they can have a core-shell structure with different porosities inside the particle, thereby ensuring sufficient porosity, enhancing the bioactivity, and at the same time, improving the strength of the particle itself.

Specifically, when the whole particle has uniform porosity, as the porous structure is introduced even to the outermost side of the particle, the strength of the particle is weakened, whereas the porous inorganic particle of one embodiment has a structure where the core close to the center of the particle has high porosity, and also the outer shell of the particle farther from the center of the particle has a porosity lower than that of the core, which can improve the strength of the particle.

The porous inorganic particle of one embodiment may include a sintered body of calcium-based particles. The calcium-based particles refer to particles containing a calcium element, and may be composed of calcium element alone or a mixture of calcium element and other element.

More specifically, the calcium-based particles may include hydroxyapatite. The hydroxyapatite is a calcium phosphate component that is an inorganic substance constituting the teeth and bone of the human body, has high biostability and promotes natural collagen production, which leads to a fundamental wrinkle improvement effect.

The calcium-based particles may contain a first calcium-based particle having a maximum diameter of 10 nm to 500 nm, or 10 nm to 400 nm, or 10 nm to 300 nm, 10 nm to 250 nm, or 100 nm to 500 nm, or 100 nm to 400 nm, or 100 nm to 300 nm, 100 nm to 250 nm, or 150 nm to 500 nm, or 150 nm to 400 nm, or 150 nm to 300 nm, 150 nm to 250 nm, and a second calcium-based particle having a maximum diameter of 1 μm to 10 μm, or 1 μm to 5 μm, or 1 μm to 3 μm, or 2 μm to 10 μm, or 2 μm to 5 μm, or 2 μm to 3 μm. That is, the calcium-based particles may include two types of particles together which are divided by the maximum diameter of the particle.

The diameter of the calcium-based particles means the distance between two points where a straight line passing through the center of gravity of the particle meets the outermost boundary line of the particle, wherein the largest value of such diameters corresponds to the maximum diameter. Examples of specific methods for measuring the maximum diameter of the calcium-based particles are not particularly limited, but can be confirmed, for example, through TEM or SEM images.

As the calcium-based particles include two types of particles divided by the maximum particle diameter in this way, it is possible to have a core-shell structure with different porosities inside the particle, thereby securing sufficient porosity to enhance bioactivity and also improving the strength of the particles themselves.

The shape of the calcium-based particles is not particularly limited, and various shapes of conventionally known hydroxyapatite can be applied without limitation. Examples of the shape of the calcium-based particles include a spherical shape, a rod shape, a needle shape, a linear shape, a plate shape, a sheet shape and the like. Examples of specific methods for measuring the shape of the calcium-based particles is not particularly limited, but can be confirmed, for example, through TEM or SEM images.

However, to give an example, the shapes of the first calcium-based particles and the second calcium-based particles may be spherical. When the shape of the first calcium-based particles having a maximum diameter of 10 nm to 500 nm is spherical, the porous inorganic particle can be produced in a spherical shape during production by a spray drying method.

Further, when the shape of the second calcium-based particles having a maximum diameter of 1 μm to 10 μm is not spherical, the surface roughness of the secondary calcium-based particles increases, which may causes a problem that a high injection force is required when injected into the body.

The content of the second calcium-based particles may be 2 parts by weight to 10 parts by weight, or 2 parts by weight to 5 parts by weight, or 3 parts by weight to 10 parts by weight, or 3 parts by weight to 5 parts by weight with respect to 1 part by weight of the first calcium-based particles.

When the content of the second calcium-based particles is excessively reduced to less than 2 parts by weight with respect to 1 part by weight of the first calcium-based particles, there is a limitation that the formation of the core by the second calcium-based particles is not sufficient, which makes it difficult to secure a high specific surface area of the porous inorganic particle core, and thus the porous inorganic particle cannot be produced in a spherical shape.

Meanwhile, when the content of the second calcium-based particles is excessively increased to more than 10 parts by weight with respect to 1 part by weight of the first calcium-based particles, there is a limitation in that formation of pores by the second calcium-based particles becomes excessive, and thus, formation of the shell layer by the first calcium-based particles becomes insufficient and the particle strength becomes weak.

The sintered body of the calcium-based particles refers to a product obtained by subjecting an aggregate of multiple calcium-based particles to a high-temperature sintering step. The sintering refers to a phenomenon in which, when a powder, which is an aggregate of multiple particles, is heated to a temperature equal to or less than the melting point, the powder melts, adheres to each other and solidifies. That is, the porous inorganic particles correspond to secondary particles obtained through sintering of calcium-based powder in which a large number of the calcium-based primary particles are gathered.

Meanwhile, the porous inorganic particle may include pores distributed in the sintered body. As the pores are distributed in the sintered body of the calcium-based particles, the porous inorganic particle may exhibit porosity. More specifically, the pores may be distributed inside and/or on the surface of the sintered body of the calcium-based particles.

The pore means an empty space inside the sintered body of calcium-based particles, and can be used to mean pore, hollow, hole, void, or the like. As used herein, the term "porous particles" may refer to particles which have pores inside and/or on the surface of the particles.

As the porous inorganic particle contains pores distributed in the sintered body, the biological activity of the sintered body is improved due to the increase in surface area due to pores, and a high skin improvement effect can be exhibited rapidly.

As will be described later, the pores may be derived from a sintering process of the calcium-based particles. Specifically, the pores correspond to spaces which are formed between the calcium-based particles by adjusting sintering conditions during sintering between the calcium-based particles.

At this time, the porous inorganic particle may have a core-shell structure of a core having a high porosity and a shell having a porosity lower than that of the core. Based on the radius, which is the distance from the center of gravity of the porous inorganic particle to the outermost boundary line of the particle, a region within a point that becomes 90%, or 80%, or 70%, or 60%, or 50% of the radial diameter starting from the center of gravity of the porous inorganic particle may be defined as the core. In addition, the remaining area outside the core can be defined as a shell.

Specifically, the porous inorganic particle may have a core thickness of 10 μm to 45 μm, or 10 μm to 42 μm, or 10 μm to 40 μm, or 10 μm to 22 μm, or 10 μm to 20 μm. The core thickness of the porous inorganic particle means the distance between two points where a straight line passing through the center of gravity of the porous inorganic particle meets the outermost side surface of the core. The core thickness of the porous inorganic particle can be obtained by SEM. When the core thickness of the porous inorganic particle is not constant, the arithmetic average value of the maximum and minimum thickness values can be calculated as the thickness of the shell layer.

As the above-mentioned core thickness range is satisfied, the porous inorganic particle can sufficiently secure the porosity of the core. When the thickness of the core is excessively reduced, it is difficult to secure the porosity.

Specifically, the core diameter of the porous inorganic particle may be 20 μm to 90 μm, or 20 μm to 84 μm, or 20 μm to 80 μm, or 20 μm to 44 μm, or 20 μm to 40 μm. The core diameter of the porous inorganic particle means the distance between two points where a straight line passing through the center of gravity of the core inside the porous inorganic particle meets the outermost boundary line of the core, wherein the largest value of such diameters corresponds to the maximum diameter. Examples of specific methods for measuring the core diameter of the porous inorganic particle is not particularly limited, but can be confirmed, for example, through SEM images. The core diameter of the porous inorganic particle corresponds to a value of about twice the above-mentioned core thickness.

As the above-mentioned core diameter range is satisfied, the porous inorganic particle can sufficiently secure the porosity by the core. If the core diameter is excessively reduced, it is difficult to secure the porosity.

The shell thickness of the porous inorganic particle may be 0.1 μm to 25 μm, or 0.1 μm to 20 μm, or 0.1 μm to 15 μm, or 0.1 μm to 10 μm, or 1 μm to 25 μm, or 1 μm to 20 μm, or 1 μm to 15 μm, or 1 μm to 10 μm, or 2 μm to 25 μm, or 2 μm to 20 μm, or 2 μm to 15 μm, or 2 μm to 10 μm. The shell thickness of the porous inorganic particle means a difference value (L1−L2) obtained by subtracting the core thickness (L2) from the distance (L1) from the center of gravity of the porous inorganic particle to a point where a straight line passing through the center of gravity meets the outermost surface of the shell. The shell thickness of the porous inorganic particle can be obtained by SEM. When the shell thickness of the porous inorganic particle is not constant, the arithmetic average value of the maximum and minimum thickness values may be calculated as the shell thickness.

As the above-mentioned shell thickness range is satisfied, the porous inorganic particle can sufficiently secure strength by the shell. When the shell thickness is excessively reduced, it is difficult to secure strength.

The porous inorganic particle may have a core diameter of 20 μm to 90 μm and a shell thickness of 0.2 μm to 50 μm.

More specifically, the porous inorganic particle have a ratio of core diameter to shell thickness (core diameter:shell thickness) of 1:1 to 100:1, or 2:1 to 100:1, or 5:1 to 100:1, or 7:1 to 100:1. Within such a range, it is possible to secure the porosity by the core and secure the strength by the shell at the same time.

The porosity of the shell may be lower than that of the core. As shown in FIGS. 1 and 2, the porous inorganic particle obtained according to the present disclosure have many pores distributed in the core, thereby ensuring excellent biological activity, and they have relatively fewer pores in a shell than in the core, or exhibit non-porosity without pores, thereby securing excellent strength.

This is considered to be because, in the spray drying for producing the porous inorganic particles, the second calcium-based particles having a maximum diameter of 1 μm to 10 μm constitute the core skeleton of the porous inorganic particle, and the first calcium-based particles having the maximum diameter of 10 nm to 500 nm, which is smaller than the maximum diameter of the second calcium-based particle, move to the outside of the porous inorganic particle core skeleton to form a shell, so that the core mostly consists of the second calcium-based particles, and the shell consists of the second calcium-based particles and the first calcium-based particles.

Specifically, the core may have a porosity of 60% to 80%, and the shell may have a porosity of 0% to 60%. The porosity was analyzed using SEM images.

Meanwhile, 70 vol. % or more of the whole first calcium-based particles may be included in the shell. The porous inorganic particles include first calcium-based particles and second calcium-based particles, wherein 70 vol. % or more, or 80 vol. % or more, or 90 vol. % or more, or 100 vol. % or less, or 70 vol. % to 100 vol. %, or 80 vol. % to 100 vol. %, or 90 vol. % to 100 vol. % of the whole first calcium-based particles may be present in the shell.

70 vol. % or more of the whole first calcium-based particles being present in the shell is defined as meaning that the first calcium-based particles are mostly presented in the shell, and specifically, 70 vol. % or more of the whole first calcium-based particles can be confirmed by measuring the volume of the whole first calcium-based particles.

Whether the first calcium-based particles and the second calcium-based particles are present in the specified area is determined by whether each of the first calcium-based particles or the second calcium-based particles are present in the specified area, and is determined by excluding particles which are present over the boundary of the specific area.

Conversely, 30 vol. % or less, or 20 vol. % or less, or 10 vol. % or less, or 0 vol. % or more, or 0 vol. % to 30 vol. %, or 0 vol. % to 20 vol. %, or 0 vol. % to 10 vol. % of the whole second calcium-based particles may be present in the shell.

Meanwhile, 70 vol. % or more of the whole second calcium-based particles may be included in the core. The porous inorganic particles include first calcium-based particles and second calcium-based particles, wherein 70 vol. % or more, or 80 vol. % or more, or 90 vol. % or more, or 100 vol. % or less, or 70 vol. % to 100 vol. %, or 80 vol. % to 100 vol. %, or 90 vol. % to 100 vol. % of the whole second calcium-based particles may be present in the core.

70 vol. % or more of the whole second calcium-based particles are being present in the core is defined as meaning that the second calcium-based particles are mostly present in the core, and specifically, 70 vol. % or more of the whole second calcium-based particles can be confirmed by measuring the volume of the whole second calcium-based particles.

Conversely, 30 vol. % or less, or 20 vol. % or less, or 10 vol. % or less, or 0 vol. % or more, or 0 vol. % to 30 vol. %, or 0 vol. % to 20 vol. %, or 0 vol. % to 10 vol. % of the whole first calcium-based particles may be present in the core.

The porous inorganic particle of the embodiment may include a shell containing 70 vol. % or more of the whole first calcium-based particles and a core containing 70 vol. % or more of the whole second calcium-based particles. As described above, in the porous inorganic particle, the second calcium-based particles may be mainly distributed in the core, and the first calcium-based particles may be mainly distributed in the shell layer.

Meanwhile, the porous inorganic particles may include a resultant product of heat treatment of the composite particles containing a biocompatible binder, first calcium-based particles, and second calcium-based particles. By heat-treating the composite particles containing the biocompatible binder, the first calcium-based particles, and the second calcium-based particles, the biocompatible binder is removed by thermal decomposition, and partial sintering of the calcium-based particles proceeds, whereby fine pores can be introduced inside the calcium-based particles. The contents concerning the first calcium-based particle and the second calcium-based particle may include all of those described above.

The weight average molecular weight of the biocompatible binder may be 100000 g/mol to 200000 g/mol, or 140000 g/mol to 190000 g/mol. In the present specification, the weight average molecular weight means a weight average molecular weight in terms of polystyrene measured by GPC method. In the process of determining the weight average molecular weight in terms of polystyrene measured by the GPC method, a commonly known analyzing device, a detector such as a refractive index detector, and an analytical column can be used. Commonly applied conditions for temperature, solvent, and flow rate can be used. Specifically, the measurement was performed, for example, using Waters PL-GPC220 and a Polymer Laboratories PLgel MIX-B 300 mm length column. An evaluation temperature was 160° C., 1,2,4-trichlorobenzene is used as a solvent, and the flow rate is 1 mL/min. The sample at a concentration of 10 mg/10 mL is supplied in an amount of 200 μL, and the values of Mw are obtained using a calibration curve formed using a polystyrene standard. 9 kinds of the polystyrene standards were used with the molecular weight of 2,000/10,000/30,000/70,000/200,000/700,000/2,000,000/4,000,000/10,000,000.

The biocompatible binder may include one or more polymers selected from the group consisting of polyvinyl alcohol, polyvinylpyrrolidone, carboxymethylcellulose, and polyethylene glycol. That is, the biocompatible binder may include polymers that are polyvinyl alcohol, polyvinylpyrrolidone, carboxymethylcellulose, polyethylene glycol, or a mixture of two or more thereof.

In one more specific example, the biocompatible binder can be polyvinyl alcohol. The polyvinyl alcohol has a boiling point of 228° C. and can be removed while vaporizing at a temperature of 228° C. or more.

Therefore, the heat treatment of the composite particle may include subjecting the composite particles to first heat treatment at a temperature of 450° C. to 550° C. and subjecting them to second heat treatment at a temperature of 600° C. to 1200° C. In the process of subjecting the composite particles to first heat treatment at a temperature of 450° C. to 550° C., or 480° C. to 520° C., the biocompatible binder is vaporized and removed by thermal decomposition.

More specifically, in the first heat treatment, the temperature is increased to a temperature of 450° C. to 550° C., or 480° C. to 520° C. at a heating rate of 2° C./min to 8° C./min, or 4° C./min to 6° C./min, and then heat treatment can be performed at a temperature of 450° C. to 550° C., or 480° C. to 520° C. for 1 hour to 3 hours.

Further, in the process of subjecting the composite particles to secondary heat treatment at a temperature of 600° C. to 1200° C., or 600° C. to 1000° C., the sintering of the composite particles including pores and calcium-based particles proceeds, so that the sintered body of the above-mentioned calcium-based particles and porous inorganic particles including pores distributed in the sintered body can be formed.

If the sintering temperature is excessively reduced to less than 600° C. in the process of the secondary heat treatment, it is difficult to secure sufficient strength of the sintered body, and if the sintering temperature is excessively increased to more than 1200° C., all pores may be removed and non-porous inorganic particles may be formed.

More specifically, in the secondary heat treatment, the temperature may be increased to a temperature of 600° C. to 1200° C. at a heating rate of 2° C./min to 8° C./min, or 4° C./min to 6° C./min, and then heat treatment may be performed at a temperature of 600° C. to 1200° C. for 1 hour to 3 hours.

Meanwhile, the content of the calcium-based particles may be 30 parts by weight or more, or 40 parts by weight or more, or 50 parts by weight or more, or 100 parts by weight or less, or 90 parts by weight or less, or 80 parts by weight or less, or 70 parts by weight or less, or 60 parts by weight or less, or 30 parts by weight part to 100 parts by weight, or 40 parts by weight to 100 parts by weight, or 50 parts by weight to 100 parts by weight, or 30 parts by weight to 90 parts by weight, or 40 parts by weight to 90 parts by weight, or 50 parts by weight to 90 parts by weight, or 30 parts by weight to 80 parts by weight, or 40 parts by weight to 80 parts by weight, or 50 parts by weight to 80 parts by weight, or 30 parts by weight to 70 parts by weight, or 40 parts by weight to 70 parts by weight, or 50 parts by weight to 70 parts by weight, or 30 parts by weight to 60 parts by weight, or 40 parts by weight to 60 parts by weight, or 50 parts by weight to 60 parts by weight with respect to 1 part by weight of the biocompatible binder.

At this time, the content of the calcium-based particles means the total content of the first calcium-based particles and the second calcium-based particles.

If the content of the calcium-based particles is excessively increased with respect to 1 part by weight of the biocompatible binder, composite particles are hardly formed during spray-drying due to the relative decrease in the weight of the binder. On the other hand, if the content of the calcium-based particles is excessively reduced with respect to 1 part by weight of the biocompatible binder, the strength of the composite particles after sintering is low due to the relative decrease in the weight of the calcium-based particles, which makes it difficult to maintain the shape and may distort the shape of the particles.

More specifically, the content of the first calcium-based particles may be 5 parts by weight to 30 parts by weight, or 5 parts by weight to 20 parts by weight, or 5 parts by weight to 15 parts by weight with respect to 1 part by weight of the biocompatible binder. Further, the content of the second calcium-based particles may be 35 parts by weight to 100 parts by weight, or 35 parts by weight to 50 parts by weight, or 35 parts by weight to 45 parts by weight with respect to 1 part by weight of the biocompatible binder.

Further, the content of the second calcium-based particles may be 2 to 10 parts by weight, or 2 to 5 parts by weight, or 3 to 10 parts by weight, or 3 to 5 parts by weight with respect to 1 part by weight of the first calcium-based particles.

Meanwhile, the composite particles containing the biocompatible binder, the first calcium-based particles, and the second calcium-based particles may be a spray-dried product of a composition containing the biocompatible binder, the first calcium-based particles, and the second calcium-based particles. The spray-dried product refers to a product obtained by spray-drying a composition containing a biocompatible binder, first calcium-based particles, and second calcium-based particles. The spray drying has fast particle production speed, does not require a further drying steps to have high productivity, does not use organic solvents and thus is produced by a safe spray drying method without a risk of explosion, thereby maximizing production efficiency.

Thus, it can have significant effect advantages over the emulsion method, which is another production method that can be used for particle formation. This is because the emulsion method has limitations in that an oil or an organic solvent must be further used to form the emulsion, and washing and drying steps must be accompanied, thereby reducing the productivity.

The shape of the composite particle is not particularly limited, but may be spherical as an example. Examples of specific methods for measuring the shape of the composite particle are not particularly limited, but can be confirmed, for example, through SEM images An average value of the maximum diameter of the composite particles may be 1 µm to 100 µm. The diameter of the composite particles means the distance between two points where a straight line passing through the center of gravity of the particle meets the boundary line of the particle, wherein the largest value of these diameters corresponds to the maximum diameter. In addition, the value obtained by measuring the maximum diameter of the multiple composite particles and calculating the arithmetic average of them is referred to as the average value of the maximum diameter. Examples of specific methods for measuring the maximum diameter of the composite particles are not particularly limited, but can be confirmed, for example, through SEM images.

The composite particle may be a group of individual particles having an average value of maximum diameter of 1 µm to 100 µm, and the individual particles included in this group may have an average maximum diameter of 1 µm to 100 µm. More specifically, 95% or 99% of the individual particles included in the group may have a maximum diameter of 1 µm to 100 µm.

The shape of the porous inorganic particles is not particularly limited, but may be spherical as an example. Examples of specific method for measuring the shape of the porous inorganic particle is not particularly limited, but can be confirmed, for example, through SEM images. As the shape of the porous inorganic particles satisfies a spherical shape, it can be injected into the body with a low injection force and induce a low immune response in the body.

In addition, the specific surface area of the porous inorganic particle may be more than 0.1 $m^2/g$, or 0.5 $m^2/g$ or more, or 1 $m^2/g$ or more, or 3 $m^2/g$ or more, or 4 $m^2/g$ or more, or 5 $m^2/g$ or more, or 10 $m^2/g$ or less, or more than 0.1 $m^2/g$ and 10 $m^2/g$ or less, or 0.5 $m^2/g$ to 10 $m^2/g$, or 1

$m^2/g$ to 10 $m^2/g$, or 3 $m^2/g$ to 10 $m^2/g$, or 4 $m^2/g$ to 10 $m^2/g$, or 5 $m^2/g$ to 10 $m^2/g$. The specific surface area was measured using a BET analyzer. As the specific surface area of the porous inorganic particle satisfies the above range, the porosity and specific surface area are higher than those of conventional high-density solid particles, and thus improved in the bioactivity, which realizes the effect of quickly inducing the treatment effect of the filler. On the other hand, when the specific surface area of the porous inorganic particles is excessively reduced to 0.1 $m^2/g$ or less or the like, the porosity and specific surface area are low like conventional high-density solid particles, and bioactive activity is reduced, and the treatment effect of the filler is reduced, which may cause a problem of requiring a large number of particles. Further, if the specific surface area of the porous inorganic particles is excessively increased, the strength of the inorganic particle sintered body is lowered, which may cause a problem that the usable process is limited in the production of the composite filler.

In addition, the total pore volume of the porous inorganic particles may be 0.001 $cm^3/g$ or more, or 0.01 $cm^3/g$ or more, or 0.013 $cm^3/g$ or more, or 0.015 $cm^3/g$ or more, or 0.05 $cm^3/g$ or less, or 0.001 $cm^3/g$ to 0.05 $cm^3/g$, or 0.01 $cm^3/g$ to 0.05 $cm^3/g$, or 0.013 $cm^3/g$ to 0.05 $cm^3/g$, or 0.015 $cm^3/g$ to 0.05 $cm^3/g$. The total pore volume means the total volume of the whole pores contained in the porous inorganic particle, and was measured using a BET analyzer. As the total pore volume of the porous inorganic particles satisfies the above range, the porosity and specific surface area are higher than those of conventional high-density solid particles, and thus the bioactivity is improved, which realizes the effect of quickly inducing the treatment effect of the filler. On the other hand, when the total pore volume of the porous inorganic particles is excessively reduced to less than 0.001 $cm^3/g$, the porosity and specific surface area are low like conventional high-density solid particles, and thus the bioactive activity is reduced, and the treatment effect of the filler is reduced, which may cause a problem of requiring a large amount of particles. In addition, when the total pore volume of the porous inorganic particles is excessively increased, the strength of the inorganic particle sintered body is lowered, which may cause a problem that the usable process is limited in the production of the composite filler.

In addition, the average value of the maximum diameter of the porous inorganic particles may be 1 µm to 1000 µm, or 10 µm to 100 µm, or 10 µm to 45 µm, or 40 µm to 1000 µm, or 40 µm to 100 µm, or 40 µm to 45 µm. The diameter of the porous inorganic particles means the distance between two points where a straight line passing through the center of gravity of the particle meets the boundary line of the particle, wherein the largest value of these diameters corresponds to the maximum diameter. In addition, the value obtained by measuring the maximum diameter of the multiple porous inorganic particles and calculating the arithmetic average of them is referred to as the average value of the maximum diameter. Examples of specific methods for measuring the maximum diameter of the composite particles are not particularly limited, but can be confirmed, for example, through SEM images.

The porous inorganic particles may be a group of individual particles having an average maximum diameter of 1 µm to 1000 µm, or 10 µm to 100 µm, or 10 µm to 45 µm, or 40 µm to 1000 µm, or 40 µm to 100 µm, or 40 µm to 45 µm, and the individual particles included in this group may have an average maximum diameter of 1 µm to 1000 µm, or 10 µm to 100 µm, or 10 µm to 45 µm, or 40 µm to 1000 µm, or 40 µm to 100 µm, or 40 µm to 45 µm. More specifically, 95% or 99% of the individual particles included in the group may have a maximum diameter of 1 µm to 1000 µm, or 10 µm to 100 µm, or 10 µm to 45 µm, or 40 µm to 1000 µm, or 40 µm to 100 µm, or 40 µm to 45 µm.

As the average value of the maximum diameter of the porous inorganic particles satisfies the above range, the skin improvement effect can be maximized without side effects in the body and pain during treatment. If the average value of the maximum diameter of the porous inorganic particles is excessively reduced to less than 1 µm, there is a possibility of causing a problem of excessive foreign matter reaction in the body. On the other hand, if the average value of the maximum diameter of the porous inorganic particle is excessively increased to more than 1000 µm, not only the specific surface area per particle mass decreases, which reduces the effect of the treatment, but also a problem of inducing great pain during treatment may occur.

Meanwhile, the porous inorganic particles have a compressive strength of 20 MPa or more, or 21 MPa or more, or 22 MPa or more, or 30 MPa or more, or 35 MPa or more, or 100 MPa or more, or 70 MPa or more, or 20 MPa to 100 MPa, or 21 MPa to 100 MPa, or 22 MPa to 100 MPa, or 30 MPa to 100 MPa, or 35 MPa to 100 MPa, or 20 MPa to 70 MPa, or 21 MPa to 70 MPa, or 22 MPa to 70 MPa, or 30 MPa to 70 MPa, or 35 MPa to 70 MPa.

The compressive strength is defined as a load per unit area when the porous inorganic particle is broken by receiving a compressive force in a single direction in a uniaxial compression test, and examples of the method and apparatus for measuring this are not particularly limited, and a conventional method for measuring a compressive strength of fine particles can be applied without limitation. In one example, the compressive strength can be measured through micro-compression device.

As the porous inorganic particles have a compressive strength that satisfies the above range, the shape of the particles can be stably maintained through high strength. On the other hand, if the compressive strength is excessively reduced to less than 20 MPa, etc., the particle strength is low, which makes it difficult to maintain the shape, and can distort the particle shape.

2. Composite Filler

According to another embodiment of the disclosure, a composite filler comprising the porous inorganic particle of one embodiment and a biodegradable carrier can be provided.

The present inventors have found through experiments that in the case of the composite filler of another embodiment, it includes the porous inorganic particles of one embodiment together with a biodegradable carrier, combine the stability of the biodegradable carrier and the biological activity of the porous inorganic particles, overcomes the limitation of single-component filler, and maintains an initial volume and then produces natural collagen through tissue stimulation of calcium particles, thereby exhibiting the effect of improving skin itself, and completed the present disclosure.

In particular, the porous inorganic particle not only has higher porosity and specific surface area than those of existing high-density solid particles, and is improved in biological activity to quickly induce the treatment effect of fillers, but also has fast particle production speed, does not require a further drying step processes to have high productivity, does not use organic solvents and thus is produced by a safe spray drying method without a risk of explosion, thereby maximizing production efficiency.

As the porous inorganic particle contained in the composite filler of another embodiment include a sintered body of calcium-based particles and pores distributed in the sintered body as described above, it has an effect of improving the bioactivity and rapidly exhibiting skin improvement effects. The contents concerning the porous inorganic particle include all of those described above in the embodiment.

Meanwhile, the composite filler may include a biodegradable carrier. The biodegradable carrier acts as a substrate, matrix or carrier of the composite filler, and the porous inorganic particle may be dispersed inside or outside the biodegradable carrier as described below.

Examples of the biodegradable carrier are not particularly limited, and various biodegradable carriers widely used in the field of fillers can be applied without limitation. To give an example, the biodegradable carrier includes gelatin, hyaluronic acid (HA), carboxymethyl cellulose (CMC), chondroitin (sulphate), dextran (sulphate), chitosan, collagen, carboxymethyl chitin, fibrin, pullulan, polylactide, polyglycolide (PGA), polylactide-glycolide copolymer (PLGA), polyanhydride, polyorthoester, polyetherester, polycaprolactone, polyethylene glycol (PEG), cyclodextrin, poloxamer, or a mixture of two or more thereof.

Preferably, hyaluronic acid may be included as the biodegradable carrier. The hyaluronic acid is a biosynthetic natural substance that is abundantly present in the skin of animals and the like, and is a hydrophilic substance because of having a large number of hydroxyl groups (—OH), and acts as a moisturizing agent in the skin of animals and the like. The hyaluronic acid is also present in the human skin and has a moisturizing effect, so it is often included in cosmetics. The hyaluronic acid reacts with the CD44 protein expressed in various epithelial cells to regulate various physiological effects.

The composite filler may include 1 to 50 parts by weight, 1 to 30 parts by weight, or 1 to 10 parts by weight of the porous inorganic particles with respect to 100 parts by weight of the biodegradable carrier. When the content of the porous inorganic particles is excessively reduced with respect to 100 parts by weight of the biodegradable carrier, skin improvement effect due to biological activity may not appear. In addition, if the content of the porous inorganic particles is excessively increased with respect to 100 parts by weight of the biodegradable carrier, porous inorganic particles in the composite filler may be unevenly dispersed, which may cause difficulties in smooth injection into the body.

Meanwhile, the composite filler may have a bioactivity of 15 mg/(kg·g) or more, or 16 mg/(kg·g) or more, or 17 mg/(kg·g) or more, or 18 mg/(kg·g) or more, or 19 mg/(kg·g) or more, or 100 mg/(kg·g) or less, or 15 mg/(kg·g) to 100 mg/(kg·g), or 16 mg/(kg·g) to 100 mg/(kg·g), or 17 mg/(kg·g) to 100 mg/(kg·g), or 18 mg/(kg·g) to 100 mg/(kg·g), or 19 mg/(kg·g) to 100 mg/(kg·g) according to the following Equation 1.

$$\text{Bioactivity} = \qquad\qquad\qquad\qquad [\text{Equation 1}]$$

$$\{[\text{Content of ion (either calcium ion or phosphorus ion)}$$
$$\text{in body fluid (mg/kg)}] -$$
$$[\text{Content of ion (either calcium ion or phosphorus ion)}$$
$$\text{in body fluid after immersing}$$
$$\text{the composite filler in the body fluid for 8 days (mg/kg)}\}$$
$$/(\text{Content of inorganic particles (g) in the composite filler}).$$

As the bioactivity of the composite filler satisfies the above range according to Equation 1, the filter has improved bioactivity, exhibits skin improvement effects rapidly, and enables maintenance of initial volume and corrective procedures.

Meanwhile, if the bioactivity according to Equation 1 is excessively reduced to less than 15 mg/(kg g), or the like, there is a drawback that the biological activity is low and the skin improvement effect is exhibited slowly.

More specifically, the composite filler may have a bioactivity of 21 mg/(kg·g) or more, or 22 mg/(kg·g) or more, or 23 mg/(kg·g) or more, or 25 mg/(kg·g) or more, or 28 mg/(kg·g) or more, or 29 mg/(kg·g) or more, or 100 mg/(kg·g) or less, or 21 mg/(kg·g) to 100 mg/(kg·g), or 22 mg/(kg·g) to 100 mg/(kg·g), or 23 mg/(kg·g) to 100 mg/(kg·g), or 25 mg/(kg·g) to 100 mg/(kg·g), or 28 mg/(kg·g) to 100 mg/(kg·g), or 29 mg/(kg·g) to 100 mg/(kg·g) according to the following Equation 2.

$$\text{Bioactivity} = \{[\text{Content of calcium ion in body fluid}\,(\text{mg/kg})] - \{\text{Content of calcium ion in body fluid after immersing the composite filler in the body fluid for 8 days}\,(\text{mg/kg})]\} / (\text{Content of inorganic particles}\,(\text{g})\,\text{in the composite filler}). \quad \text{[Equation 2]}$$

Further, the composite filler may have a bioactivity of 15 mg/(kg·g) or more, or 16 mg/(kg·g) or more, or 17 mg/(kg·g) or more, or 18 mg/(kg·g) or more, or 19 mg/(kg·g) or more, or 21 mg/(kg·g) or more, or 22 mg/(kg·g) or more, or 100 mg/(kg·g) or less, or 15 mg/(kg·g) to 100 mg/(kg·g), or 16 mg/(kg·g) to 100 mg/(kg·g), or 17 mg/(kg·g) to 100 mg/(kg·g), or 18 mg/(kg·g) to 100 mg/(kg·g), or 19 mg/(kg·g) to 100 mg/(kg·g), or 21 mg/(kg·g) to 100 mg/(kg·g), or 22 mg/(kg·g) to 100 mg/(kg·g) according to the following Equation 3.

$$\text{Bioactivity} = \{[\text{Content of phosphorus ion in body fluid}\,(\text{mg/kg})] - \{\text{Content of phosphorus ion in body fluid after immersing the composite filler in the body fluid for 8 days}\,(\text{mg/kg})]\} / (\text{Content of inorganic particles}\,(\text{g})\,\text{in the composite filler}). \quad \text{[Equation 3]}$$

Meanwhile, the composite filler may further contain various additive components commonly included in fillers, for example, a lubricant such as glycerin, a phosphate buffer, and the like, if necessary.

3. Product

According to another embodiment of the disclosure, there can be provided a product including the composite filler of the other embodiment. The contents concerning the composite filler includes all of those described above in the other embodiment.

Examples of the product are not particularly limited, and can be applied without limitation depending on the purpose of applying the filler. Examples of the products include food, pharmaceuticals, cosmetics, and the like.

Advantageous Effects

According to the present disclosure, a porous inorganic particle having high production efficiency and excellent bioactivity and strength, and a composite filler and product using the same can be provided.

BRIEF DESCRIPTION OF THE DRAWINGS

FIG. 1 shows surface and cross-section SEM images of porous inorganic particles obtained in Example 1.

FIG. 2 shows surface and cross-section SEM images of porous inorganic particles obtained in Example 2.

FIG. 3 shows surface and cross-section SEM images of porous inorganic particles obtained in Comparative Example 1.

FIG. 4 shows surface and cross-section SEM images of porous inorganic particles obtained in Comparative Example 2.

Hereinafter, the invention is described in more detail with reference to the following examples. However, these examples are for illustrative purposes only, and are not intended to limit the subject matter of the present disclosure.

EXAMPLE

Example 1

(1) Production of Porous Inorganic Particles

Polyvinyl alcohol (PVA, weight average molecular weight: 146,000~186,000 Da, 99+% hydrolyzed) was stirred in water at 90° C. to prepare a 1 wt. % PVA aqueous solution.

Spherical hydroxyapatite (HAp) powder (1st HAp) having a maximum diameter of 200 nm and spherical hydroxyapatite (HAp) powder (2nd HAp) having a maximum diameter of 2.5 μm were added to a PVA aqueous solution so that the weight ratio of 1st HAp/2nd HAp/PVA satisfies 10/40/1 to prepare a suspension.

The suspension is spray-dried (Buchi mini spray dryer B-290). When drying was completed, particles were obtained, placed in a crucible, maintained at 500° C. for 2 hours in a box furnace to remove PVA, and then sintered at 1000° C. for 2 hours to produce a porous inorganic particle.

(2) Production of Composite Filler 0.4 g of the porous inorganic particle was mixed with 9.6 g of hyaluronic acid to produce a composite filler.

Example 2

A porous inorganic particle and a composite filler were produced in the same manner as in Example 1, except that the sintering temperature was changed to 1200° C. as shown in Table 1 below.

COMPARATIVE EXAMPLE

Comparative Example 1

A porous inorganic particle and a composite filler were produced in the same manner as in Example 2, except that spherical hydroxyapatite (HAp) powder (2nd HAp) having a maximum diameter of 2.5 μm was added at a weight ratio of the 1st HAp/2nd HAp/PVA of 0/50/1 without using the 1st HAp as shown in Table 1 below.

Comparative Example 2

A porous inorganic particle and a composite filler were produced in the same manner as in Example 2, except that needle-shaped hydroxyapatite (HAp) powder (1st HAp) having a maximum diameter of 150 nm was added at a weight ratio of the 1st HAp/2nd HAp/PVA of 12/0/1 without using the 2nd HAp as shown in Table 1 below.

Experimental Example

The physical properties of the inorganic particles and composite fillers obtained in the Examples and Comparative Examples were measured by the following methods, and the results are shown in Table 1, Table 2 and Figures.

1. Particle Shape

The surface and cross-section shapes of the inorganic particles obtained in the Examples and Comparative Examples were confirmed through SEM images, which are shown in FIGS. 1 to 4, respectively.

2. Particle Size

For the inorganic particles obtained in the Examples and Comparative Examples, the maximum diameter of each 100 particles was measured through SEM images, and the arithmetic mean of these values was calculated.

3. Porosity

For the inorganic particles obtained in the Examples and Comparative Examples, the shape of the particle cross section was confirmed through SEM images, and the porosity was expressed as follows according to the presence or absence of pores.

○: presence of pores on the cross-section SEM image inside the particle

X: absence of pores on the cross-section SEM image inside the particle

4. Specific Surface Area and Total Pore Volume

The specific surface area and total pore volume of the inorganic particles obtained in the Examples and Comparative Examples were measured using a BET analyzer.

5. Particle Strength

The compressive strength of the inorganic particles obtained in the Examples and Comparative Examples was measured using a micro-compression device, which was evaluated as particle strength.

As shown in Table 1, it was confirmed that in the case of inorganic particles contained in the composite fillers of Examples, the porous inorganic particle having pores inside the particles were obtained, and both the specific surface area and the pore volume were significantly improved as compared to Comparative Example 2. Further, it was confirmed that in the case of the inorganic particles contained in the composite fillers of Examples was obtained, the compressive strength of the porous inorganic particle was 22 MPa to 38 MPa, which was significantly improved as compared to Comparative Example 1.

On the other hand, it was confirmed that the compressive strength of the porous inorganic particle contained in the composite filler of Comparative Example 1 was 15 MPa which was reduced as compared to Examples. In addition, it was confirmed that in the case of inorganic particles contained in the composite filler of Comparative Example 2, non-porous inorganic particles with no pores inside the particles were obtained, 6. Bioactivity After immersing the composite filler obtained in the Examples and Comparative Examples in simulated body fluid for 8 days, a sample was prepared by acid digestion method, the content of Ca ions and P ions in the sample (unit: mg/kg) were measured using an ICP-OES device, and the bioactivity was evaluated by the following Equation 1. The content of Ca ions and P ions in the simulated body fluid was measured to be 42 mg/kg, which means that the larger the value of the following Equation 1, the better the bioactivity.

$$\text{Bioactivity} = \qquad\qquad\qquad\text{[Equation 1]}$$

$$\{[\text{Content of ion (either calcium ion or phosphorus ion)}$$
$$\text{in body fluid (mg/kg)}] -$$
$$[\text{Content of ion (either calcium ion or phosphorus ion)}$$
$$\text{in body fluid after immersing}$$
$$\text{the composite filler in the body fluid for 8 days (mg/kg)}\}$$
$$/(\text{Content of inorganic particles (g) in the composite filler}).$$

TABLE 1

Experimental Example Measurement Results of Examples and Comparative Examples

| Category | Weight ratio of 1st HAp/2nd HAp/PVA | Maximum diameter and shape of 1st HAp | Maximum diameter and shape of 2nd HAp | Sintering temperature | Particle shape | Particle size (μm) | Porosity | Specific surface area (m²/g) | Total pore volume (cm³/g) | Compressive strength (MPa) |
|---|---|---|---|---|---|---|---|---|---|---|
| Example 1 | 10/40/1 | 200 nm Spherical | 2.5 μm Spherical | 1000° C. | FIG. 1 | 42 | ○ | 5 | 0.0155 | 22 |
| Example 2 | 10/40/1 | 200 nm Spherical | 2.5 μm Spherical | 1200° C. | FIG. 2 | 44 | ○ | 4 | 0.0131 | 38 |
| Comparative Example 1 | 0/50/1 | — | 2.5 μm Spherical | 1200° C. | FIG. 3 | 34 | ○ | 4 | 0.0123 | 15 |
| Comparative Example 2 | 12/0/1 | 150 nm needle shape | — | 1200° C. | FIG. 4 | 49 | X | 0.1 | 0.0009 | 75 |

TABLE 2

| | Category | |
|---|---|---|
| Experimental Example Measurement Results of Examples and Comparative Examples | | |
| | Ca ion bioactivity (mg/(kg · g)) | P ion bioactivity (mg/(kg · g)) |
| Example 1 | 29.2 | 22.2 |
| Example 2 | 27.8 | 19.4 |
| Comparative Example 1 | 27.8 | 20.8 |
| Comparative Example 2 | 20.8 | 12.5 |

As shown in Table 2, it was confirmed that in the case of the composite filler of Example 1, Ca ion bioactivity was 29.2 mg/(kg·g) and the Pion bioactivity was 22.2 mg/(kg·g), which were larger than those of Comparative Examples, and thus excellent in the bioactivity. On the other hand, the composite filler of Example 2 exhibited the same level of bioactivity as Comparative Example 1, and exhibited improved bioactivity compared to Comparative Example 2.

The invention claimed is:

1. A porous inorganic particle comprising:
a sintered body of calcium-based particles, pores distributed in the sintered body, and
a core-shell structure of a core having a high porosity and a shell having a porosity lower than that of the core,
wherein the calcium-based particles comprise first calcium-based particles having a maximum diameter of 10 nm to 500 nm, and second calcium-based particles having a maximum diameter of 1 μm to 10 μm.

2. The porous inorganic particle of claim 1, wherein:
a content of the second calcium-based particles is 2 parts by weigh to 10 parts by weight with respect to 1 part by weight of the first calcium-based particles.

3. The porous inorganic particle of claim 1, wherein:
70 vol. % or more of the entire first calcium-based particles is contained in the shell.

4. The porous inorganic particle of claim 1, wherein:
70 vol. % or more of the entire second calcium-based particles is contained in the core.

5. The porous inorganic particle of claim 1, wherein:
the porous inorganic particle has a core diameter of 20 μm to 90 μm and a shell thickness of 0.2 μm to 50 μm.

6. The porous inorganic particle of claim 1, wherein:
the porous inorganic particle has a ratio of a core diameter to a shell thickness (core diameter:shell thickness) of 1:1 to 100:1.

7. The porous inorganic particle of claim 1, wherein:
the porous inorganic particle has a total pore volume of at least 0.001 cm³/g.

8. The porous inorganic particle of claim 1, wherein:
the porous inorganic particle has a specific surface area of more than 0.1 m²/g.

9. The porous inorganic particle of claim 1, wherein:
the porous inorganic particle has a compressive strength of at least 20 MPa.

10. The porous inorganic particle of claim 1, wherein:
the first calcium-based particles and the second calcium-based particles each have spherical shapes.

11. The porous inorganic particle of claim 1, wherein:
the first calcium-based particles and the second calcium-based particles each comprise hydroxyapatite.

12. The porous inorganic particle of claim 1, wherein:
the porous inorganic particle comprises the resultant product of heat treatment of composite particles containing a biocompatible binder, the first calcium-based particles, and the second calcium-based particles.

13. The porous inorganic particle of claim 12, wherein:
the biocompatible binder comprises one or more polymers selected from the group consisting of polyvinyl alcohol, polyvinylpyrrolidone, carboxymethylcellulose, and polyethylene glycol.

14. The porous inorganic particle of claim 12, wherein:
the heat treatment of the composite particles comprises,
subjecting the composite particles to first heat treatment at a temperature of 450° C. to 550° C., and
subjecting them to second heat treatment at a temperature of 600° C. to 1200° C.

15. The porous inorganic particle of claim 12, wherein:
a content of the first calcium-based particles is 5 parts by weight to 30 parts by weight with respect to 1 part by weight of the biocompatible binder.

16. The porous inorganic particle of claim 12, wherein:
a content of the second calcium-based particles is 35 parts by weight to 100 parts by weight with respect to 1 part by weight of the biocompatible binder.

17. A composite filler comprising the porous inorganic particle of claim 1 and a biodegradable carrier.

18. The composite filler of claim 17, wherein:
the composite filler has a bioactivity of at least 15 mg/(kg·g) according to the following Equation 1:

Bioactivity={[Content of ion (either calcium ion or phosphorus ion) in body fluid (mg/kg)]–[Content of ion (either calcium ion or phosphorus ion) in the body fluid after immersing a composite filler in the body fluid for 8 days (mg/kg)]}/(Content of inorganic particles (g) in the composite filler).                    [Equation 1]

19. The composite filler of claim 17, wherein:
the biodegradable carrier comprises hyaluronic acid.

20. A product comprising the composite filler of claim 17.

* * * * *